United States Patent
Hanko et al.

(10) Patent No.: US 9,568,450 B2
(45) Date of Patent: Feb. 14, 2017

(54) MEASURING ARRANGEMENT AND METHOD FOR REGISTERING AN ANALYTE CONCENTRATION IN A MEASURED MEDIUM

(75) Inventors: Michael Hanko, Dresden (DE); Thomas Wilhelm, Waldheim (DE)

(73) Assignee: Endress+Hauser Conducta GmbH+Co. KG, Gerlingen (DE)

(*) Notice: Subject to any disclaimer, the term of this patent is extended or adjusted under 35 U.S.C. 154(b) by 744 days.

(21) Appl. No.: 13/816,091

(22) PCT Filed: Aug. 8, 2011

(86) PCT No.: PCT/EP2011/063579
§ 371 (c)(1),
(2), (4) Date: Apr. 25, 2013

(87) PCT Pub. No.: WO2012/019980
PCT Pub. Date: Feb. 16, 2012

(65) Prior Publication Data
US 2013/0213807 A1    Aug. 22, 2013

(30) Foreign Application Priority Data

Aug. 10, 2010  (DE) .................. 10 2010 033 936
May 20, 2011  (DE) .................. 10 2011 102 699

(51) Int. Cl.
*G01N 27/416*  (2006.01)
*G01N 27/333*  (2006.01)
(Continued)

(52) U.S. Cl.
CPC ........ *G01N 27/416* (2013.01); *G01N 27/4167* (2013.01); *G01N 27/30* (2013.01);
(Continued)

(58) Field of Classification Search
CPC .................................................. G01N 27/403
(Continued)

(56) References Cited

U.S. PATENT DOCUMENTS 6,120,676 A * 9/2000 Heller ................. A61B 5/1411
                                                    205/775
2007/0214872 A1* 9/2007 Ammann ........... G01N 27/4165
                                                     73/53.01
2008/0190782 A1   8/2008 Lavastre

FOREIGN PATENT DOCUMENTS

CN      101184992 A    5/2008
CN      101765766 A    6/2010
WO   WO 2008/154409 A1 * 12/2008 ........... G01N 27/403

OTHER PUBLICATIONS

Schaepman (LabPlus International, Oct. 2005).*
(Continued)

*Primary Examiner* — Luan Van
*Assistant Examiner* — Steven E Rosenwald
(74) *Attorney, Agent, or Firm* — Christopher R. Powers; PatServe

(57) ABSTRACT

A measuring arrangement for registering an analyte concentration in a measured medium includes a three electrode arrangement having a working electrode, a reference electrode and a counter electrode. The working electrode includes an analyte-insensitive, redox mediator, and the reference electrode a pH-sensitive electrode. The counter electrode can be formed of an inert, electrically conductive material. The measuring arrangement can be embodied to provide a desired voltage between the working electrode and the reference electrode and to register the electrical current flowing, in such case, through the measured medium, between the counter electrode and the working electrode.

19 Claims, 4 Drawing Sheets

(51) Int. Cl.
  *G01N 27/49* (2006.01)
  *G01N 27/30* (2006.01)
  *G01N 27/48* (2006.01)

(52) U.S. Cl.
  CPC ......... *G01N 27/302* (2013.01); *G01N 27/333* (2013.01); *G01N 27/48* (2013.01); *G01N 27/49* (2013.01)

(58) Field of Classification Search
  USPC ....................................................... 257/253
  See application file for complete search history.

(56) References Cited

OTHER PUBLICATIONS

Bard and Faulkner (Electrochemical Methods, John Wiley & Sons, 1980).*
Allen J. Bard and Larry R. Faulkner, "Electrochemical Methods, Fundamentals and Applications", 2001.
English translation of IPR, Feb. 21, 2013, WIPO, Geneva.
International Search Report, Nov. 8, 2011, The Netherlands.
Bard et al, Eds "Electrochemical Dictionary" Library of Congress Control No. 2007941793, pp. 673.
Bard et al., "Electrochemical Methods Fundamental and Applications" John Wiley & Sons, Inc., 2rd edition.

\* cited by examiner

MEASURING ARRANGEMENT AND METHOD FOR REGISTERING AN ANALYTE CONCENTRATION IN A MEASURED MEDIUM

TECHNICAL FIELD

The invention relates to a measuring arrangement and to a method for registering an analyte concentration, especially a pH-value, in a measured medium.

BACKGROUND DISCUSSION

The most well-known ion-selective electrode and that most frequently applied in such potentiometric sensors as measuring half-cell is the pH-glass electrode. The glass electrode includes, as a rule, a tubular housing, which is closed on one end by a membrane of a pH-sensitive glass and which is filled with an inner electrolyte, for example, a chloride containing, buffer solution, into which a potential sensing element, for example, a chloridized silver wire, extends. In contact with the measured medium, there forms on the glass membrane a measuring half-cell potential dependent on the pH-value. Serving as reference half-cell, as a rule, is a reference electrode of the second type, for example, an Ag/AgCl- or calomel-electrode, with a liquid junction between, on the one hand, a half-cell space containing the reference electrolyte and, on the other hand, the measured medium. The potential difference between the measuring half-cell potential tappable on the potential sensing element of the measuring half-cell and the reference potential of the reference half-cell (the reference potential of the reference half-cell is ideally independent of the pH-value of the measured medium) forms the measurement signal of the measuring transducer and is a direct measure for the H+-ion activity, respectively the pH-value, of the measured medium.

The measuring of analyte concentrations, especially the measuring of pH-value, which reflects the concentration of $H^+$-ions in the measured medium, plays an important role in environmental analytics and in chemical or biochemical methods in the laboratory or in industrial process measurements technology. Analytes include, for example, certain ion types or other chemical compounds dissolved in the measured medium. Electrochemical analytical methods, such as, for example, voltammetry or potentiometry register, as a rule, the analyte activity, from which the analyte concentration can be derived. In dilute solutions, to a first approximation, the analyte activity can be set equal to the analyte concentration.

A special case of activity, or concentration, measurement is the measuring of the pH-value. The pH-value corresponds to the negative base-10 logarithm of the $H^+$-ion activity in the measured medium, which in dilute solutions can be set equal to the $H^+$-ion concentration.

For measuring ion concentrations or pH-value both in the laboratory as well as also in process analytics, frequently potentiometric sensors are used. These have, as a rule, a measuring half-cell with an ion-selective electrode as measuring half-cell, which includes, for example, an ion-selective glass-, solid- or polymer membrane. The relative change of the equilibrium Galvani voltage between a measured medium and a potential sensing electrode of the measuring half-cell is essentially effected by the activity change predominantly of the kind of ion to be determined. Referenced to a reference potential of a reference half-cell of essentially constant potential, e.g. a reference electrode of second type, such as the Ag/AgCl-reference electrode, the sought ion concentration or the pH-value of the measured medium can be determined by means of a high-impedance voltmeter with high accuracy and little apparatus complexity. Serving as measurement signal of such a sensor is thus the potential difference between the measuring- and reference half-cells. Ion selective electrodes are described, for example, in "Ion-Selective Electrodes", J. Koryta and K. Stulik, Cambridge University Press, 1983, Pg. 61 or in "Das Arbeiten mit ionenselektiven Elektroden (Working with Ion-Selective Electrodes)", K. Cammann, H. Galster, Springer, 1996.

The most well-known ion-selective electrode and that most frequently applied in such potentiometric sensors as measuring half-cell is the pH-glass electrode. The glass electrode includes, as a rule, a tubular housing, which is closed on one end by a membrane of a pH-sensitive glass and which is filled with an inner electrolyte, for example, a chloride containing, buffer solution, into which a potential sensing element, for example, a chloridized silver wire, extends. In contact with the measured medium, there forms on the glass membrane a measuring half-cell potential dependent on the pH-value. Serving as reference half-cell, as a rule, is a reference electrode of second type, for example, an Ag/AgCl- or calomel-electrode, with a liquid junction between, on the one hand, a half-cell space containing the reference electrolyte and, on the other hand, the measured medium. The potential difference between the measuring half-cell potential tappable on the potential sensing element of the measuring half-cell and the reference potential of the reference half-cell (the reference potential of the reference half-cell is ideally independent of the pH-value of the measured medium) forms the measurement signal of the measuring transducer and is a direct measure for the $H^+$-ion activity, respectively the pH-value, of the measured medium.

Although such potentiometric sensors assure very precise and reliable measurement results and are well established both in the laboratory—as well as also in process analytics, they have a number of disadvantages. For example, a series of defects or degradation phenomena of the reference electrodes of the second type serving as reference half-cell can occur to degrade the quality of the measuring. Thus, the potential of such reference half-cells tends in practice generally to drift, i.e. to undergo a slow, however, ongoing, change of the reference potential. Moreover, the inner electrolyte of the reference half-cell can escape or dry out. The liquid junction, via which a reference half-cell of the second type is in contact with the measured medium, can become blocked by solids, especially difficultly soluble salts, and electrode poisons can get into the reference half-cell via the liquid junction. Due to the small conductivity of the pH-sensitive glass membrane, it is additionally required to measure the potential difference between the half-cells with very high impedance, a fact which can lead to instabilities in the measuring and to measured value corruptions. Due to the high resistance of the glass of the glass membrane, limits are set on the miniaturization of such sensors. Thus, in the case of a lessening of the glass membrane area, the resistance of the measuring half-cell becomes ever greater. There is, therefore, already long the need for alternative, more robust sensor principles, which should preferably work without one of the conventional reference electrodes of second type.

Described in WO 2005/066618 A1 is a sensor for determining an analyte concentration in a measured medium in a bore hole. The sensor includes a working electrode and a counter electrode as well as an external, reference electrode. Bound on the surface of the working electrode are two or more different molecular species R and M, wherein the molecular species M is sensitive to the analyte L to be determined, for example, binds the analyte L, while the molecular species R is insensitive to the analyte L.

The analyte concentration in the measured medium can be ascertained with this sensor by registering a rectangular wave voltammogram, also referred to as a (linear) square wave voltammogram, SWV. Depending on whether the voltage between working electrode and counter electrode is increased or decreased during the registering of the voltammogram, there occurs on the working electrode an oxidation or a reduction of the molecular species R and M. These oxidation- or reduction processes show up in the plots of the electrical current flowing through the working electrode during the registering of the voltammogram as a function of the associated voltage value as (local) electrical current maxima, or (local) electrical current minima, also referred to as electrical current peaks. When in the following maxima, minima or extrema are discussed, unless indicated otherwise, local maxima, minima or extrema are meant.

If present on the working electrode are, respectively, a molecular species R and a molecular species M, there results, assuming that the voltage range of the voltammogram is selected appropriately broadly, respectively a first extremum associated with the molecular species R and a second extremum associated with the molecular species M. While the position of the extremum associated with the analyte sensitive species M changes as a function of the analyte concentration in the surrounding measured medium, the position of the extremum associated with the analyte-insensitive species R is independent of the analyte concentration of the measured medium. The extremum associated with the species R can, thus, serve as an additional, internal reference, so that measurement uncertainties due to degeneration effects of the external reference electrode can be recognized and/or prevented.

Similarly embodied sensors are also known from WO 2005/085825 A1 and WO 2008/154409 A1.

SUMMARY OF THE INVENTION

It is an object of the invention to provide a measuring arrangement, which permits a stable measuring, with little drift, of an analyte concentration, especially an $H^+$-ion concentration or a therefrom derived, pH-value. Especially, the measuring arrangement should work without an external, conventional reference electrode.

This object is achieved by a measuring arrangement for registering an analyte concentration in a measured medium, wherein the measuring arrangement comprises a three electrode arrangement having a working electrode, a reference electrode and a counter electrode, wherein the working electrode includes an analyte-insensitive redox mediator, and the reference electrode an analyte sensitive electrode.

The counter electrode can comprise, for example, an inert, electrically conductive material, such as platinum or carbon.

The measuring arrangement can be embodied to provide a predetermined desired voltage between the working electrode and the reference electrode, and to register, in such case, the electrical current flowing through the measured medium between the counter electrode and the working electrode.

The measuring arrangement can include, for example, a control circuit, especially a potentiostatic, control circuit, which is embodied to provide between the working electrode and the reference electrode a desired voltage and to register, in such case, the electrical current flowing between the working electrode and the counter electrode. For example, the measuring arrangement can be embodied to bring about the predetermined desired voltage between the working electrode and the reference electrode by controlling an electrical current flowing through the measured medium between the counter electrode and the working electrode, while the working electrode, the counter electrode and the reference electrode are in electrically conductive contact with the measured medium. For this, the measuring arrangement can comprise a potentiostat, which has a corresponding electronic control circuit. The measuring arrangement or the potentiostat can especially be embodied to perform, by means of the three electrode arrangement, amperometric, for example, voltammetric, measurements. An example of voltammetric measurement is linear sweep voltammetry (LSV), in the case of which a direct voltage ramp is placed between the working electrode and reference electrode, i.e. in the case of which a voltage $U_{meas}$ applied between the working electrode and reference electrode (compare FIG. 1) is varied as a linear function of time. Other examples of voltammetric measurements include: staircase voltammetry, which corresponds to the LSV, wherein, however, the rise, or the fall, of the voltage $U_{meas}$ applied between the working- and reference electrodes occurs in the manner of steps as a function of time; differential pulse- or difference pulse voltammetry; and rectangular wave voltammetry, also referred to as square wave voltammetry (SWV), in the case of which there are superimposed on a direct voltage ramp, rectangular pulses with amplitude, which is smaller, especially constant, in comparison to the voltage range, over which the direct voltage ramp extends. Voltammetric measuring includes, moreover, cyclic voltammetry, also referred to as the triangular voltage method, in the case of which the voltage $U_{meas}$ applied between working- and reference electrodes is varied in a first step as a linearly rising function of time, and in a thereon following, second step as a linearly falling function of time, wherein output- and end values of the voltage $U_{meas}$ are identical in such a cycle. The electrical current I flowing between the counter electrode and the working electrode in the case of a predetermined voltage $U_{meas}$, or in the case of a predetermined curve of the voltage $U_{meas}$, is registered as a function of time, or as a function of the voltage $U_{meas}$. A plotting of the electrical current curve I as a function of the voltage $U_{meas}$ is referred to as a cyclic voltammogram. Details, for this, are provided, for example, in A. J. Bard, L. R. Faulkner, Electrochemical Methods, Fundamentals and Applications, John Wiley & Sons, New York, 2001, especially Chapters 6 and 7.

A redox mediator is a chemical substance, which is capable of reversible release and acceptance of electrons. This means, that a redox mediator can reversibly, especially in a plurality of oxidation reduction cycles following one another, be oxidized by a first electrical potential and reduced by a second electrical potential. In a voltametric measurement, the oxidation or reduction of the redox mediator of the working electrode is shown as an electrical current extremum. The analyte sensitive electrode connected here as reference electrode outputs a "reference potential" dependent on the pH-value, i.e. the reference of the three electrode arrangement, respectively the position of the zero-point of the voltametric measuring, depends on the analyte concentration present in the measured medium. Since the redox mediator is insensitive to the analyte, the potential difference $U_{meas}$ between the working- and reference electrode, at which the extremum of the electrical current is located, is a measure for the analyte concentration of the measured medium. In a special embodiment of the measuring arrangement, the analyte is $H^+$-ions, so that the pH-value of the measured medium can be ascertained from the position of the extremum relative to the zero-point specified by the pH-sensitive, reference electrode.

The measuring arrangement can include, for performing voltametric measurements, a function generator, which is embodied to specify a desired voltage curve to be provided between the working electrode and the reference electrode, wherein the measuring arrangement is embodied to register the electrical current flowing between the counter electrode and the working electrode in voltametric measuring for obtaining the desired voltage curve, for example, a voltage ramp or a triangular voltage profile. The desired voltage curve can especially exhibit, at least at times, a linear rise, a linear decline, a step-like decline, a sawtooth curve, a triangular curve, a rectangular curve or a superpositioning of these.

The function generator can be a component of an evaluating system of the measuring arrangement or be connected with an evaluating system of the measuring arrangement. The evaluating unit can comprise, for example, a data processing system with a microprocessor and a data memory, which the microprocessor can access. Especially, the data processing system can be a computer, for example, a PC, a measurement transmitter, a registering device or some other data processing system with an input/output interface and/or a display system, for example, a display.

The evaluating system can be embodied to ascertain, from an electrical current curve between the working electrode and the counter electrode registered in a voltammetric measurement, a value of the voltage lying between the working electrode and the reference electrode, at which voltage the electrical current curve has an extremum associated with an oxidation or reduction of the redox mediator, and, from this value, to derive the analyte concentration of the measured medium. Since the redox mediator is analyte-insensitive, the position, i.e. the associated voltage value, of the electrical current extremum associated with an oxidation- or reduction reaction of the redox mediator is not dependent on the analyte concentration present in the measured medium. In contrast, however, the position of the reference potential provided by the analyte sensitive, reference electrode does depend on the analyte concentration. This leads to the fact that the position of an electrical current extremum associated with an oxidation or reduction of the redox mediator in voltametric measurements with the measuring arrangement of the invention is a measure for the analyte concentration present in the measured medium. If the analyte of concern is $H^+$-ions, the evaluation system can be correspondingly embodied to derive from the corresponding extremum of the electrical current curve the pH-value of the measured medium.

The redox mediator can be selected from the group containing: Prussian, or Berlin, blue (iron(III)-hexacyanoferrate (II/III)), analogs of Prussian, or Berlin, blue, derivatives of Prussian, or Berlin, blue, ferrocene, ferrocene analogs, ferrocene derivatives, ferroin, the redox system $Ce^{3+}/Ce^{4+}$ and the redox system $I^-/I_2$.

The redox mediator can be immobilized on an electrically conductive surface of the working electrode, for example, by bonding it, especially covalently, to the surface of the working electrode. Alternatively, the redox mediator can be present on the surface in the form of a difficultly soluble precipitate.

The electrically conductive surface of the working electrode can also be coated with a polymer layer, which covers and protects the redox mediator present on the surface of the working electrode. The redox mediator can also be bound in a polymer film, especially an electrically conductive, polymer film, applied on the electrically conductive surface of the working electrode.

The working electrode can, in an alternative embodiment, comprise an inner electrolyte accommodated in a housing, into which electrolyte there extends a potential sensing element connected with a working electrode connection of the measuring arrangement, especially connected, in the case in which the measuring arrangement has a potentiostat, with the working electrode connection of the potentiostat, wherein the inner electrolyte is in electrically conductive contact with the measured medium via a liquid junction, especially a porous diaphragm. In this embodiment, the redox mediator can, as above described, be immobilized on a surface of the potential sensing element and/or be present dissolved in the inner electrolyte. This construction of the working electrode makes one think of the construction of reference electrodes of second type, which are used, as a rule, in potentiometric measuring chains, or combination electrodes, for measuring an analyte concentration or a pH-value, with the above mentioned disadvantages. While, however, in the case of a potentiometric measuring chain, the potential of the reference electrode is dependent on the salt concentration present in the inner electrolyte, and, thus, in the case of depletion of salt in the inner electrolyte, the potential drifts, the position of the electrical current extrema associated with the oxidation, or reduction, of the redox mediator in the case of the here described working electrode is independent of the redox mediator concentration. So long as redox mediator is present on a surface of the potential sensing element or in the inner electrolyte solution, there is no drift.

The inner electrolyte can in an embodiment be present as liquid, especially as an aqueous solution. Alternatively, the inner electrolyte can be present as a hydrogel. The inner electrolyte can in an additional, alternative embodiment comprise an ionic liquid. The redox mediator can be present dissolved in the inner electrolyte. In a preferred embodiment, the inner electrolyte has a constant ionic strength.

Serving as counter electrode can be a solid electrode of an electrically conductive, inert material, for example, of metal, especially platinum, or carbon, especially glassy carbon, doped diamond or graphite.

In an additional embodiment, the working electrode comprises an inner electrolyte accommodated in a housing. A potential sensing element connected with the working electrode connection of the measuring arrangement, especially with a potentiostat of the measuring arrangement, extends into the inner electrolyte, wherein the electrolyte is in electrically conductive contact with the measured medium via a liquid junction. Also the counter electrode can extend into the inner electrolyte.

As analyte sensitive, reference electrode, the measuring arrangement can have an ion-selective electrode having a housing sealed by an ion-selective membrane at a region intended for immersion in the measured medium. An inner electrolyte is accommodated in the housing and a potential sensing electrode extends in the electrolyte. The potential sensing electrode is connected with a connection of the measuring arrangement intended for the reference electrode, especially in the case of application of a potentiostat, with a connection of the potentiostat intended for the reference electrode. For determining the pH-value of a measured medium, the reference electrode can comprise a pH-glass electrode with a housing sealed by a pH-sensitive glass membrane at a region intended for immersion in the measured medium. Accommodated in the housing is an inner electrolyte, for example, a pH-buffer solution, into which a potential sensing electrode extends. The potential sensing electrode is connected with the connection of the measuring arrangement intended for the reference electrode, especially with the connection of the potentiostat.

Alternatively, the analyte sensitive, reference electrode can also comprise an analyte sensitive, especially pH-sensitive, ISFET-chip or a field effect transistor-chip sensitive for other analyte molecules, especially for biomolecules.

The measuring arrangement can also comprise a housing, in which a first, especially tubular, chamber is formed, which is sealed on one end by an analyte sensitive membrane, and in which a first inner electrolyte is accommodated, into which a first potential sensing element extends, which is connected with a reference electrode connection of the measuring arrangement, especially with a reference electrode connection of a potentiostat of the measuring arrangement. Formed in the housing can be furthermore a second chamber, especially a second chamber annularly surrounding the first chamber. Accommodated in the second chamber is a second inner electrolyte, into which second and third potential sensing elements extend, wherein there is arranged in the outer wall of the second chamber, in a region intended for immersion in the measured medium, a liquid junction, via which the second inner electrolyte is in electrically, or electrolytically, conductive contact with the measured medium. The second potential sensing element can be connected with a working electrode connection of the measuring arrangement. The redox mediator can be immobilized on a surface of the second potential sensing element and/or be present dissolved in the second inner electrolyte. The third potential sensing element can be connected with a counter electrode connection of the measuring arrangement, especially with a counter electrode connection of the potentiostat. The third potential sensing element can be of an inert material. For example, it can be formed of a metal such as platinum or carbon and be connected with the counter electrode connection of the measuring arrangement, especially with the counter electrode connection of the potentiostat.

The invention relates also to a method for determining an analyte concentration or a value derived therefrom, especially a pH-value, in a measured medium, wherein a working electrode, a reference electrode and a counter electrode are brought into electrically conductive contact with the measured medium, wherein the working electrode comprises an analyte-insensitive redox mediator, the counter electrode an inert material and the reference electrode an analyte sensitive electrode, and wherein a voltammetric measurement is performed, and, based on the voltammetric measurement, the analyte concentration, especially the pH-value, is ascertained.

The voltammetric measurement can comprise the registering of a linear sweep voltammogram, a difference pulse voltammogram, a square wave voltammogram or a cyclic voltammogram, wherein the analyte concentration is ascertained based on at least one electrical current extremum associated with an oxidation or a reduction of the redox mediator.

In case the analyte involves $H^+$-ions, the pH-value of the measured medium can be derived from at least one electrical current extremum associated with an oxidation or a reduction of the redox mediator.

The derivation of the analyte concentration, respectively the pH-value, can be performed, for example, by deriving from the linear sweep voltammogram, the difference pulse voltammogram, the square wave voltammogram or the cyclic voltammogram the voltage between reference electrode and working electrode belonging to at least one electrical current extremum associated with a reduction or an oxidation, and determining the analyte concentration, respectively the pH-value, from this voltage. The derivation of the analyte concentration, respectively the pH-value, can be performed by the evaluating system described above. Furnished in a memory of the evaluating system, for example, based on calibration measurements, can be an assignment rule, which associates a pH-value with a voltage belonging to an electrical current extremum ascertained from a linear sweep voltammogram or a cyclic voltammogram and associated with a reduction, or an oxidation, of the redox mediator.

This method can be performed automatically, for example, by means of the above described measuring arrangement, especially controlled by an evaluating system, which includes a data processing system, e.g. a computer or a measurement transmitter.

BRIEF DESCRIPTION OF THE DRAWINGS

The invention will now be described in greater detail based on examples of embodiments shown in the drawing, the figures of which show as follows.

DETAILED DISCUSSION IN CONJUNCTION WITH THE DRAWINGS

Figure 1:
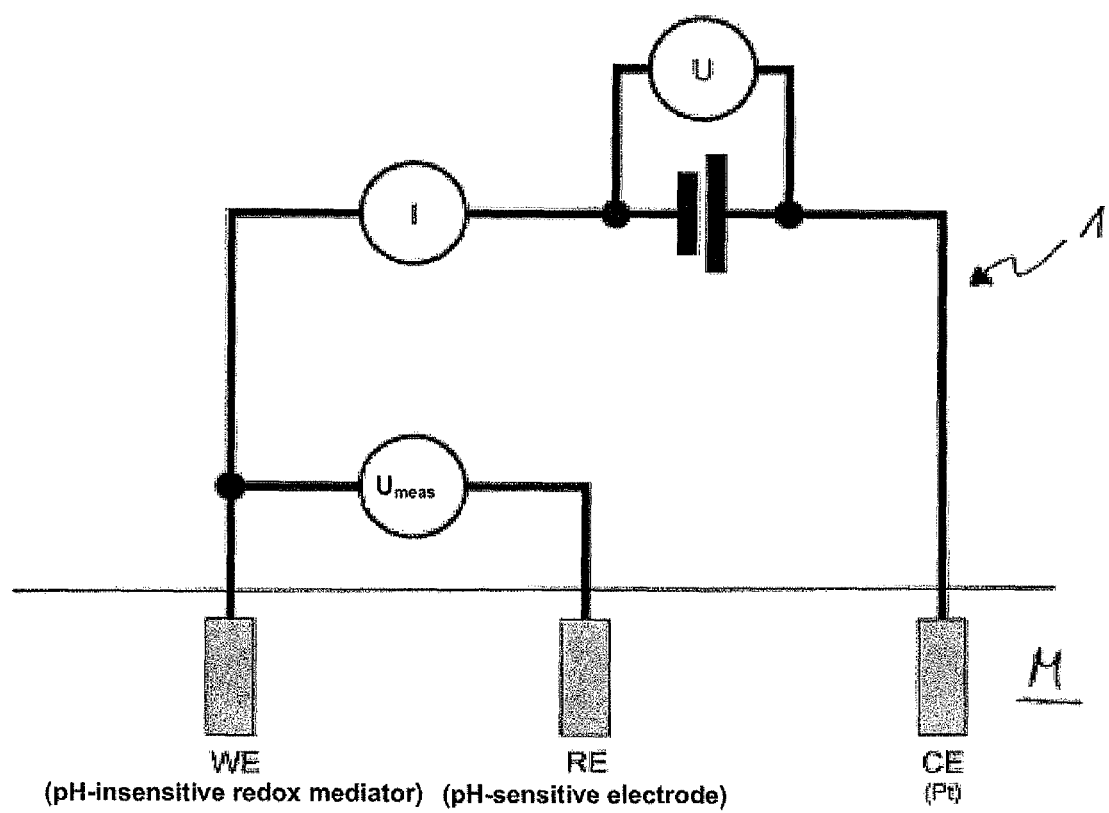
FIG. 1 is a schematic representation of a three electrode arrangement for performing a voltammetric measurement for determining an analyte concentration.

FIG. 1 shows schematically a three electrode arrangement 1 having a working electrode WE, a reference electrode RE and a counter electrode CE, all of which extend into a measured medium M. For performing a potentiostatic measurement, a predetermined voltage $U_{meas}$ is placed between the working electrode WE and the reference electrode RE. The predetermined voltage $U_{meas}$ can be a constant direct voltage; it can, however, also vary in time, so that a voltage curve $U_{meas}$, i.e. a voltage $U_{meas}$ variable as a function of time, lies between the working electrode WE and the reference electrode RE. The predetermined voltage curve $U_{meas}$ can be, for example, a direct voltage ramp, especially one linearly rising or linearly falling as a function of time, for registering a linear sweep voltammogram. In another example, the voltage $U_{meas}$ can also have a triangular direct voltage curve exhibiting a linear rise starting from a desired voltage starting value and a thereon following, linear decline back to the desired voltage starting value. Such a voltage curve $U_{meas}$ serves for registering a cyclic voltammogram.

The predetermined voltage $U_{meas}$ between the working electrode WE and the reference electrode RE is set, respectively controlled, based, for example, on an electrical current I flowing through the measured medium between the counter electrode CE and the working electrode WE. Control of the voltage lying between the working electrode WE and the reference electrode RE, or of the voltage curve lying between the working electrode WE and the reference electrode RE, to the predetermined voltage, or to the voltage curve $U_{meas}$, can occur by means of a potentiostat, which includes for this purpose an electronic control amplifier (not shown in FIG. 1). No electrical current flows through the reference electrode RE, in such case, so that the potential of the reference electrode RE remains uninfluenced by the control.

The potentiostat includes, furthermore, means for registering the electrical current, or the curve of the electrical current, I flowing between the working electrode WE and the counter electrode CE for bringing about the predetermined voltage, or the voltage curve, $U_{meas}$. The electrical current curve I can be expressed as a function of time and/or as a function of voltage $U_{meas}$. Such means can in the simplest case comprise an output, via which the electrical current I, or the electrical current curve I, is output in analog or digitized form to an evaluating system, for example, a data processing system, such as a measurement transmitter, a plotting device, a recording device or a computer. The potentiostat can also comprise a microprocessor and a data memory, which the microprocessor can access, and can process the registered electrical current I, or a signal derived from the electrical current I, especially a digitized and/or amplified signal, for example, by storing it in the data memory or outputting such via a display system or a communication interface.

If there occurs on the working electrode WE an electrochemical reaction, for example, an oxidation or reduction, the voltage actually lying between working electrode WE and reference electrode RE changes, so that between the working electrode WE and the counter electrode CE a rising or falling electrical current flowing between the working electrode and the counter electrode can be registered.

A plot of the electrical current I flowing between the counter electrode CE and the working electrode WE as a function of the predetermined voltage $U_{meas}$ lying between the working electrode WE and the reference electrode RE, which plot is referred to here as a voltammogram, includes, consequently, electrical current extrema, which are associated with electrochemical processes occurring on the working electrode. Details for evaluation of voltammograms are set forth in the above mentioned book of A. J. Bard and L. R. Faulkner.

With the three electrode arrangement 1 shown in FIG. 1, such voltammetric measurements can be performed for determining an analyte concentration of the measured medium M. In the here described example, the analyte is $H^+$-ions, so that the pH-value of the measured medium M can be derived from the voltammetric measurement. The here described measuring principle can, of course, be applied in analogous manner also for determining the concentration of another analyte.

The working electrode WE includes a pH-insensitive redox mediator. The redox mediator can, for example, be immobilized on a surface of the working electrode. As initially described, the redox mediator has the property that it can reversibly release and accept electrons.

The counter electrode CE is composed of an electrically conductive material that is inert relative to the measured medium. In the present example, it is formed of platinum.

The reference electrode RE is provided in the form of a pH-sensitive electrode, for example, a glass electrode, which comprises: a housing filled with an inner electrolyte and sealed by a pH-sensitive, glass membrane; and a potential sensing electrode extending into the inner electrolyte. Forming on the pH-sensitive, glass membrane is an interface potential, whose value depends on the pH-value of the measured medium M. In contrast to conventional voltammetric measurements, in the case of which there is used as reference electrode RE, as a rule, a stable potential, reference electrode, e.g. an Ag/AgCl-reference electrode, the glass electrode applied here yields a reference potential dependent on the pH-value of the measured medium.

Since the redox mediator of the working electrode WE is pH-insensitive, a voltammetric measurement using a stable potential, Ag/AgCl, reference electrode in the three electrode arrangement 1 would yield an electrical current extremum associated with oxidation, or reduction, of the redox mediator always at the same voltage value $U_{meas}$, independently of the pH-value of the measured medium M. Since the potential of the reference electrode RE of the three electrode arrangement 1 shown in FIG. 1 does, however, vary as a function of the pH-value of the measured medium, the "zero line" of the voltammetric measurement varies correspondingly, so that also the position of the electrical current extremum associated with a reduction or oxidation of the redox mediator varies relative to this zero line as a function of the pH-value.

Figure 2A:
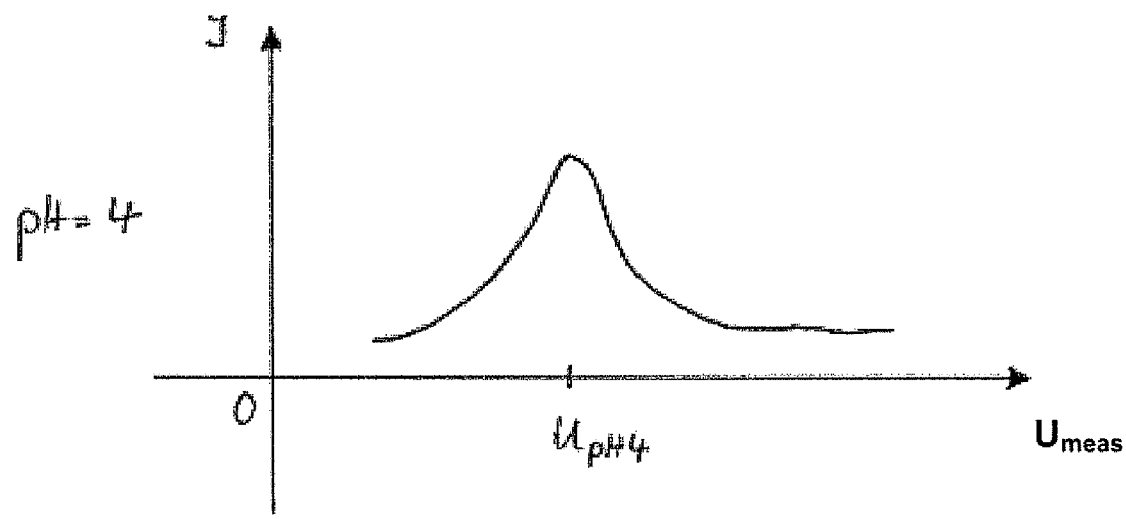
FIG. 2 shows two schematically illustrated difference pulse voltammograms for two different pH-values.
Figure 2B:
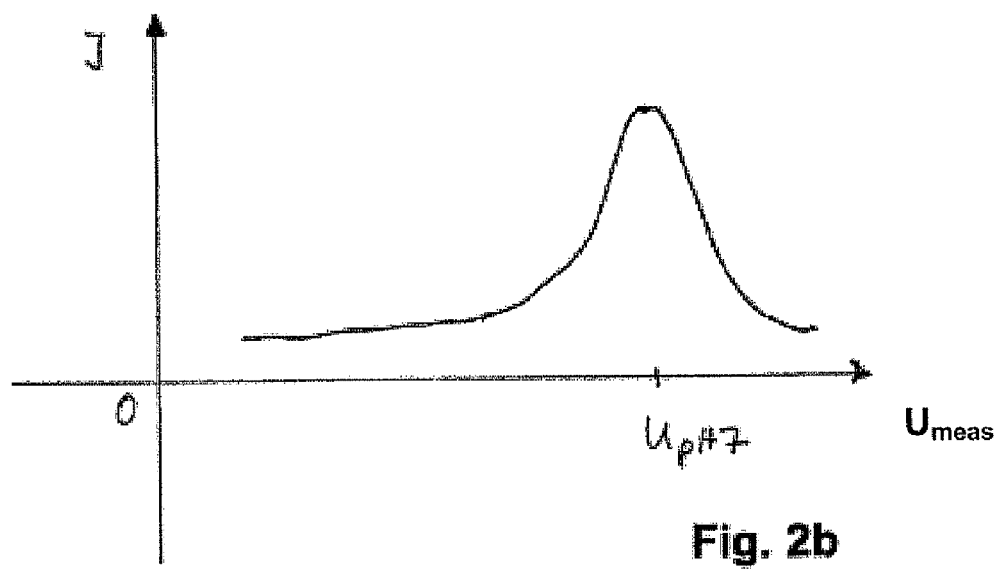

For purposes of illustration, FIG. 2 shows two different pH-values representing difference pulse voltammograms. FIG. 2a shows a difference pulse voltammogram in the case of pH 4, and FIG. 2b in the case of pH 7. Due to the variability of the reference potential as a function of the pH-value of the measured medium M, the electrical current maximum occurring due to the oxidation of the redox mediator in the LSV shifts as a function of the pH-value (here to higher voltage values $U_{meas}$). The voltage values $U_{pH4}$ and $U_{pH7}$ associated with the electrical current maximum are thus a measure for the pH-value reigning in the measured medium.

Based on calibration measurements, an assignment rule can be ascertained, which permits, especially automatically, associating a pH-value with a voltage value belonging to a particular electrical current extremum. A measuring arrangement having a three electrode arrangement 1, a potentiostatic control circuit and an evaluating unit, which is embodied to evaluate the voltammograms registered by means of the potentiostatic control circuit as described, can, thus, based on such an assignment rule furnished in a memory of the evaluating unit, determine the pH-value of the measured medium and output and/or display corresponding measured values.

Figure 3:
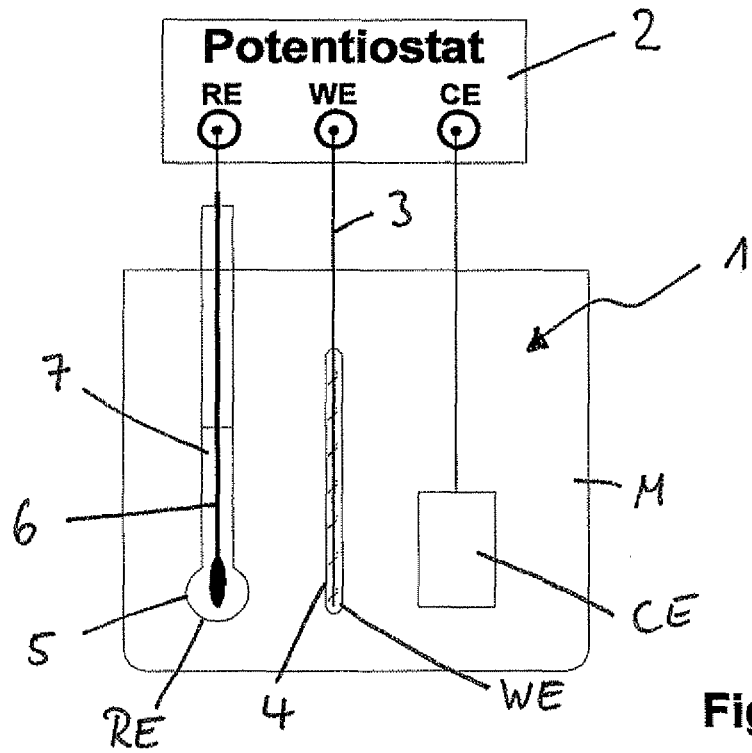
FIG. 3 is a schematic representation of a first embodiment of the measuring arrangement of the invention.

FIG. 3 shows schematically a first example of an embodiment with a three electrode arrangement of a working electrode WE, a reference electrode RE and a counter electrode CE for voltammetric determining of an analyte concentration, here a pH-value. The electrodes are connected with associated connections of a potentiostat 2, which, as above described, is embodied to apply a desired voltage or a desired voltage curve between the working electrode WE and the reference electrode RE and to register, in such case, the electrical current flowing between the working electrode WE and the counter electrode CE. The working electrode WE is formed of a platinum wire 3, which is coated with Prussian, or Berlin, blue (iron(III)-hexacyanoferrate (II/III)) as redox mediator 4. The Prussian, or Berlin, blue can be covered by a polymer layer or bound in a polymer layer. The reference electrode RE is formed in the example shown here by a glass electrode with a tubular housing sealed on one end by a pH-sensitive, glass membrane 5 and accommodating an inner electrolyte 6, into which a potential sensing electrode 7 extends. The inner electrolyte 6 can be, for example, a pH-buffered, 3 molar KCl-solution. The potential sensing electrode 7 can be, for example, a chlorided silver wire. It is connected with the reference electrode connection of the potentiostat 2. Instead of a glass electrode for the pH-sensitive, reference electrode RE, also a pH ISFET measuring transducer with a pH-sensitive, field effect transistor chip can be used. ISFET-measuring transducers can also be used for determining the concentration of other analytes, for example, chemical compounds or biomolecules. Used as analyte sensitive, reference electrode for determining ions other than $H^+$-ions are ion-selective electrodes (ISE) sensitive for the corresponding ions. The counter electrode CE is formed in the present example of a piece of platinum sheet metal.

Figure 4:
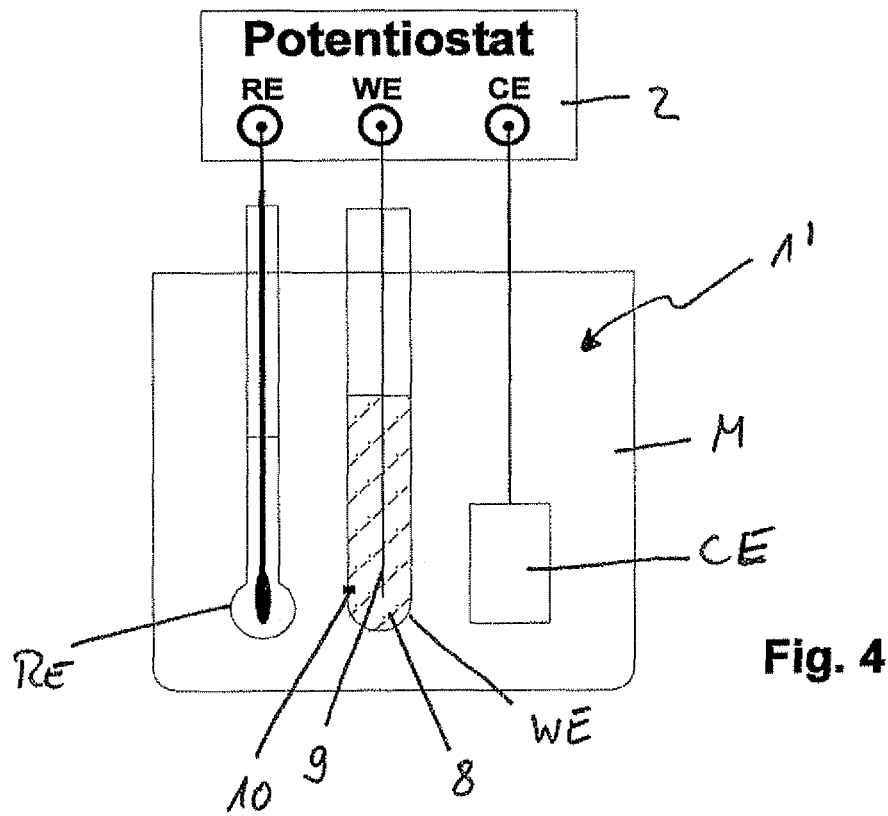
FIG. 4 is a schematic representation of a second embodiment of the measuring arrangement of the invention.

FIG. 4 shows schematically a further example of an embodiment having a three electrode arrangement 1', whose electrodes are connected with the corresponding connections of the potentiostat 2. The counter electrode CE and the reference electrode RE are embodied in equal manner to that described for the example illustrated in FIG. 3. The working electrode WE possesses in the example shown here a housing, in which an inner electrolyte 8 is accommodated, into which extends a potential sensing electrode 9 connected with the connection of the potentiostat 2 intended for the working electrode WE. The potential sensing electrode 9 can be platinum, for example. The inner electrolyte 8 is in electrically, or electrolytically, conductive contact with the measured medium M via a liquid junction 10, for example, in the form of a porous diaphragm. The redox mediator can be present in this embodiment either, as described based on FIG. 3, on a surface of the potential sensing electrode 9, or—alternatively or supplementally—it can be present dissolved in the inner electrolyte 8 of the working electrode WE. The inner electrolyte 8 can be, for example, an aqueous salt solution, however, also a highly viscous hydrogel. In the latter case, bleeding of the inner electrolyte 8 through the liquid junction 10 is effectively prevented.

Figure 5:
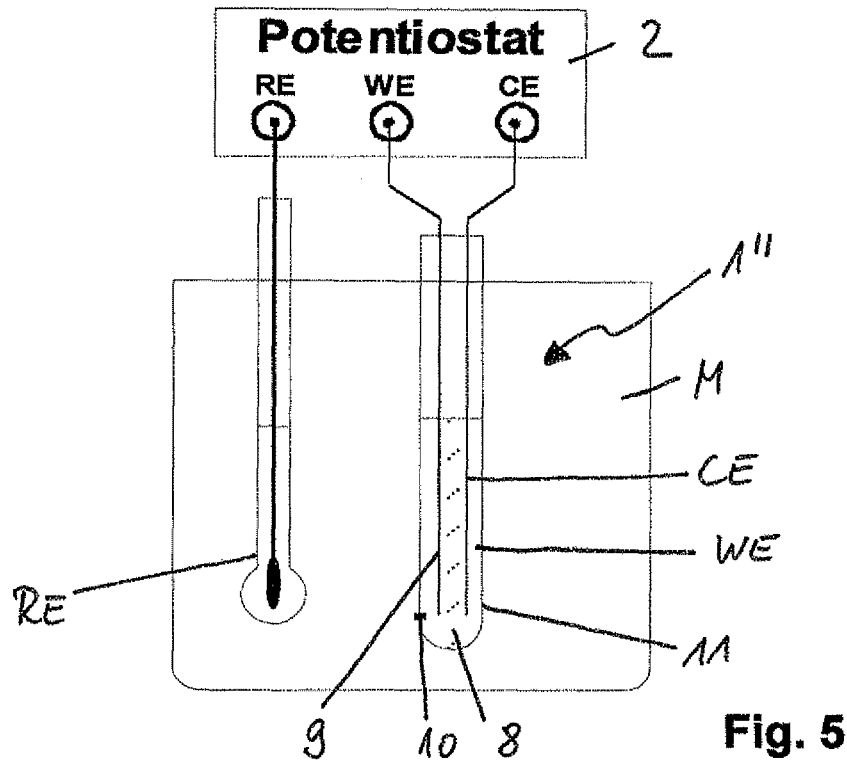
FIG. 5 is a schematic representation of a third embodiment of the measuring arrangement of the invention.

FIG. 5 shows schematically a third example of an embodiment having a three electrode arrangement 1'', whose electrodes are connected with the corresponding connections of the potentiostat 2. The reference electrode RE is embodied in equal manner to that described for the example of an embodiment illustrated in FIG. 3. The working electrode WE and the counter electrode CE are provided in a shared housing 11. Housing 11 contains an inner electrolyte 8, into which a potential sensing electrode 9 extends, which is connected with the connection of the potentiostat 2 provided for the working electrode WE. The inner electrolyte 8 is in electrically, or electrolytically, conductive contact with the measured medium M via a liquid junction 10 arranged in the housing wall of the housing 11. The redox mediator can, as also the case in the example of FIG. 4, be present either on a surface of the potential sensing electrode 9, or, alternatively or supplementally, it can be present dissolved in the inner electrolyte 8. Extending into the inner electrolyte 8 is, moreover, the counter electrode CE, which is embodied in the example shown here as a platinum wire.

Figure 6:
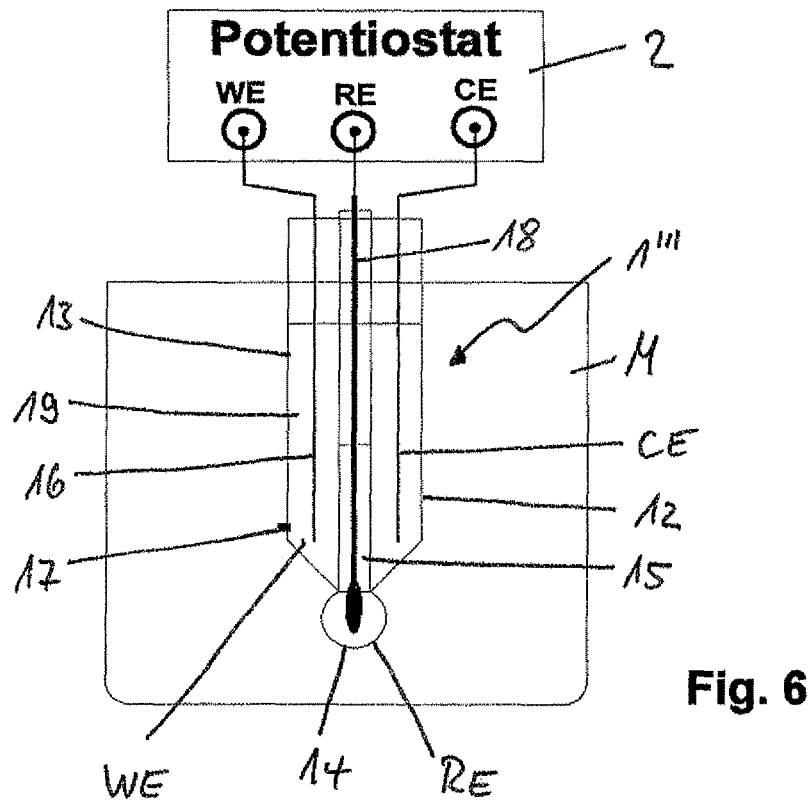
FIG. 6 is a schematic representation of a fourth embodiment of the measuring arrangement of the invention.

FIG. 6 shows schematically a fourth example of an embodiment of a three electrode arrangement 1''', which is accommodated in compact manner in a single sensor housing 12. Sensor housing 12 includes a first tubular chamber 15, in which the reference electrode RE of the three electrode arrangement 1''' is formed. Chamber 15 is sealed on its lower end by a pH-sensitive membrane 14 and contains a first inner electrolyte, for example, a pH-buffered, 3 M KCl solution. Extending into the inner electrolyte is a potential sensing element 18 connected with the reference electrode connection of the potentiostat 2. Potential sensing element 18 can be provided, for example, in the form of a chlorided silver wire.

Formed in the sensor housing 12 is a second chamber 13, which surrounds the first chamber 15 as an annular chamber, and in which are formed the working electrode WE and the counter electrode CE of the three electrode arrangement 1'''. Second chamber 13 contains a second inner electrolyte 19, into which extends a second potential sensing element 16, which is connected with the working electrode connection of the potentiostat 2. The second potential sensing element 16 can be formed of a platinum wire, on whose surface a redox mediator is applied. The redox mediator can, alternatively or supplementally, be present dissolved in the second inner electrolyte 19. The second inner electrolyte 19 is in electrically, or electrolytically, conductive contact with the measured medium M via a liquid junction 17 arranged in an outer wall of the chamber 13. Extending into the second inner electrolyte 19 is also the counter electrode CE, which is connected with the counter electrode connection of the potentiostat 2 and which can be, for example, in the form of a platinum wire.

The invention is not limited to the examples of embodiments described here. Especially, instead of the glass electrode used as reference electrode in the examples described here, also a pH-sensitive ISFET-chip, or an ion-selective electrode, suitable for measuring other ion types can be used.

The invention claimed is:

1. A measuring arrangement for registering a concentration of a certain ion in a measured medium, comprising:
   a three electrode arrangement comprising a working electrode, a reference electrode and a counter electrode; and
   a potentiostatic control circuit configured to provide a desired voltage between the working electrode and the reference electrode by supplying an electrical current flowing through the measured medium between the counter electrode and the working electrode, the potentiostatic control circuit further configured to measure and operate upon the supplied electrical current to determine the concentration of the certain ion in the measured medium,
   wherein said working electrode includes a redox mediator insensitive to said ion and said reference electrode comprises an ion-sensitive electrode sensitive to said ion, and wherein no current is supplied to the reference electrode.

2. The measuring arrangement as claimed in claim 1, wherein:
   the measuring arrangement is embodied to perform, by means of the three electrode arrangement voltammetric measurements.

3. The measuring arrangement as claimed in claim 1, further comprising:
   a function generator, which is embodied to specify a voltage curve to be produced between said working electrode and said reference electrode, wherein:
   the measuring arrangement is embodied to register the electrical current flowing through the measured medium between said working electrode and said counter electrode, as a result of the specified voltage curve, as a function of the voltage produced provided between said reference electrode and said working electrode.

4. The measuring arrangement as claimed in claim 1, further comprising:

an evaluating system, which is embodied to ascertain, from an electrical current curve between said working electrode and said counter electrode registered in the case of a voltammetric measurement, a value of the desired voltage between said working electrode and said reference electrode, at which voltage the electrical current curve has a local extremum associated with an oxidation or reduction of the redox mediator, and from this value to derive an analyte concentration in the measured medium.

5. The measuring arrangement as claimed in claim 1, wherein:
said redox mediator is selected from the group consisting of Prussian, or Berlin, blue, analogs of Prussian, or Berlin, blue, derivatives of Prussian, or Berlin, blue, ferrocene, ferrocene analogs, ferrocene derivatives, ferroin, the redox system Ce3+/Ce4+ and the redox system I−/I2.

6. The measuring arrangement as claimed in claim 1, wherein:
said redox mediator is immobilized on an electrically conductive surface of said working electrode.

7. The measuring arrangement as claimed in claim 6, wherein:
said redox mediator is bound in a polymer film arranged on the surface of the working electrode.

8. The measuring arrangement as claimed in claim 1, wherein:
said working electrode comprises an inner electrolyte accommodated in a housing, into which a potential sensing element extends, the potential sensing element connected with a working electrode connection of the measuring arrangement, and
said inner electrolyte is in electrically or electrolytically conductive contact with the measured medium via a liquid junction.

9. The measuring arrangement as claimed in claim 1, wherein:
said reference electrode comprises an inner electrolyte accommodated in a housing and an analyte sensitive membrane terminating the housing in a region provided for contact with the measured medium.

10. The measuring arrangement as claimed in claim 1, wherein:
said reference electrode comprises an ISFET-chip.

11. The measuring arrangement as claimed in claim 1, wherein:
the measuring arrangement is embodied to perform amperometric measurements via the three electrode arrangement.

12. A measuring arrangement comprising:
a three electrode arrangement comprising a working electrode, a reference electrode and a counter electrode contacting a measured medium;
a control circuit, which is embodied to provide between said working electrode and said reference electrode a desired voltage, and to register an electrical current flowing through the measured medium between said counter electrode and said working electrode needed to generate the desired voltage between said working electrode and said reference electrode without flowing a separate current through the reference electrode;
a function generator embodied to specify a desired voltage curve as a function of time to be provided between said working electrode and said reference electrode; and an evaluating system embodied to ascertain, from an electrical current curve between the working electrode and the counter electrode registered in a voltammetric measurement, a value of the voltage between the working electrode and the reference electrode, at which value the corresponding electrical current flowing through the measured medium between the working electrode and the counter electrode has an extremum associated with an oxidation or reduction of a redox mediator, and to derive an ion concentration in the measured medium from the value,
wherein said reference electrode comprises an ion-selective electrode, and said working electrode includes the redox mediator and said redox mediator is insensitive to the ion.

13. A measuring arrangement for registering a pH-value of a measured medium, comprising:
a three electrode arrangement comprising a working electrode, a reference electrode and a counter electrode;
a potentiostatic control circuit configured to provide a desired voltage between the working electrode and the reference electrode via an electrical current provided through the measured medium between said counter electrode and said working electrode, the electrical current generating the desired voltage between said working electrode and said reference electrode with no current flowing through the reference electrode, and the potentiostatic control circuit further configured to measure the electrical current;
a function generator embodied to specify a desired voltage curve as a function of time to be provided between said working electrode and said reference electrode; and
an evaluating system embodied to ascertain, from an electrical current curve between the working electrode and the counter electrode registered in a voltammetric measurement, a value of the voltage between the working electrode and the reference electrode, at which value the corresponding electrical current flowing between the working electrode and the counter electrode has an extremum associated with an oxidation or reduction of the redox mediator, and from this value of the voltage to the derive the pH-value in the measured medium,
wherein said working electrode includes a pH-insensitive redox mediator and said reference electrode comprises a pH-sensitive electrode.

14. The measuring arrangement as claimed in claim 13, wherein:
said redox mediator is selected from the group consisting of Prussian blue or Berlin blue, analogs of Prussian blue or Berlin blue, derivatives of Prussian blue or Berlin blue, ferrocene, ferrocene analogs, ferrocene derivatives, ferroin, the redox system Ce3+/Ce4+, and the redox system I−/I2.

15. The measuring arrangement as claimed in claim 13, wherein:
said reference electrode comprises a pH-buffered inner electrolyte, accommodated in a housing and an a pH-sensitive membrane terminating the housing in a region provided for contact with the measured medium; or
said reference electrode comprises a pH-sensitive ISFET chip.

16. A measuring arrangement, comprising:
a three electrode arrangement comprising a working electrode, a reference electrode and a counter electrode contacting a measured medium;

a control circuit, which is embodied to provide between said working electrode and said reference electrode a desired voltage, and to register the electrical current flowing through the measured medium between said counter electrode and said working electrode; and an evaluating system, which is embodied to ascertain from a voltammetric measurement using said three electrode arrangement a pH-value of the measured medium, wherein said reference electrode is embodied to provide a reference potential dependent on a pH-value of the measured medium, no current is supplied to the reference electrode, and said working electrode includes a pH-insensitive redox mediator.

17. A method for determining a concentration of a certain ion in a measured medium, the method comprising:

bringing a working electrode, a reference electrode and a counter electrode into electrically or electrolytically conductive contact with the measured medium, wherein the working electrode comprises a redox mediator insensitive to said ion, the counter electrode comprises an inert material, and the reference electrode comprises an ion-selective electrode sensitive to said ion, wherein no current is supplied to the reference electrode;

performing a voltammetric measurement in the measured medium; and ascertaining the concentration of said ion based on the voltammetric measurement.

18. The method according to claim 17, wherein the performing of a voltammetric measurement further comprises:

controlling by means of a potentiostatic control circuit a voltage between the working electrode and the reference electrode according to a desired voltage curve; and registering a corresponding electrical current curve of an electrical current flowing between the working electrode and the counter electrode for producing the desired voltage curve between the working electrode and the reference electrode.

19. The method according to claim 18, wherein the ascertaining the concentration of said ion further comprises:

ascertaining from said electrical current curve a value of the voltage between the working electrode and the reference electrode, at which value the corresponding electrical current flowing between the working electrode and the counter electrode has an extremum associated with an oxidation or reduction of the redox mediator; and deriving from said value the concentration of said ion.

* * * * *

UNITED STATES PATENT AND TRADEMARK OFFICE
CERTIFICATE OF CORRECTION

PATENT NO.       : 9,568,450 B2
APPLICATION NO.  : 13/816091
DATED            : February 14, 2017
INVENTOR(S)      : Michael Hanko et al.

Page 1 of 1

It is certified that error appears in the above-identified patent and that said Letters Patent is hereby corrected as shown below:

In the Claims

Claim 3 should read:
3. The measuring arrangement as claimed in claim 1, further comprising:
 a function generator, which is embodied to specify a voltage curve to be produced between said working electrode and said reference electrode, wherein:
 the measuring arrangement is embodied to register the electrical current flowing through the measured medium between said working electrode and said counter electrode, as a result of the specified voltage curve, as a function of the voltage produced between said reference electrode and said working electrode.

Signed and Sealed this
Twenty-third Day of May, 2017

Michelle K. Lee
*Director of the United States Patent and Trademark Office*